United States Patent [19]
Takayanagi et al.

[11] Patent Number: 5,846,258
[45] Date of Patent: Dec. 8, 1998

[54] INTRAOCULAR BALLOON, INSERTION GUIDE FOR INTRAOCULAR BALLOON, AND HOLDER

[75] Inventors: Yoshinori Takayanagi, 3-5, Minami Ohdori 1-chome, Kushiro-shi, Hokkaido; Kazuo Tachi, Kushiro, both of Japan

[73] Assignee: Yoshinori Takayanagi, Kushiro, Japan

[21] Appl. No.: 834,852

[22] Filed: Apr. 10, 1997

[30] Foreign Application Priority Data

Dec. 20, 1996 [JP] Japan .................................. 8-340988

[51] Int. Cl.⁶ .................................................. A61M 29/00
[52] U.S. Cl. .............................................. 606/192; 604/22
[58] Field of Search .............. 604/96–101; 606/191–195

[56] References Cited

U.S. PATENT DOCUMENTS

| | | | |
|---|---|---|---|
| 4,395,806 | 8/1983 | Wonder et al. | 606/195 |
| 4,517,979 | 5/1985 | Pacenka | 606/195 |
| 4,545,367 | 10/1985 | Tucci | 606/195 |

*Primary Examiner*—William Lewis
*Attorney, Agent, or Firm*—Oblon, Spivak, McClelland, Maier & Neustadt, P.C.

[57] ABSTRACT

The invention provides an intraocular balloon and associated devices such as an intraocular balloon insertion guide and a holder. They enable a surgeon to readily perform an operation for correcting retinal detachment and to lighten a burden imposed on a surgical patient to a great extent. The intraocular balloon is characterized by having a gas injection valve; the intraocular balloon insertion guide facilitates the insertion of the intraocular balloon into an eye; and the holder holds the intraocular balloon and the intraocular balloon insertion guide, and is fixed onto the eyeball. The invention is also directed to a surgical procedure for retinal detachment using such devices.

19 Claims, 12 Drawing Sheets

INTRAOCULAR BALLOON, INSERTION GUIDE FOR INTRAOCULAR BALLOON, AND HOLDER

BACKGROUND OF THE INVENTION

1. Field of the Invention

The present invention relates to an intraocular device used in surgical procedures for correcting retinal detachment and diabetic retinopathy which induce a gravely reduced acuity of vision and, in the worst case, blindness, and to a surgical procedure for correcting retinal detachment which uses the intraocular device.

2. Description of the Related Art

Retinal detachment is a serious disorder characterized in that the sensory retina and the pigmented epithelium of retina are detached from each other, and leads to blindness if it is not cured. FIGS. 1 to 4 schematically show a general surgical procedure for correcting lacuna-induced retinal detachment.

Figure 1:
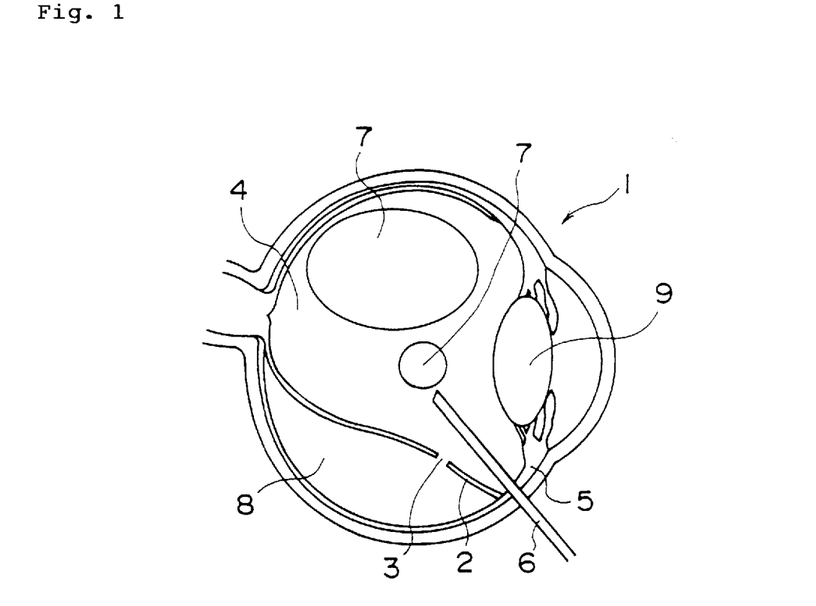
FIG. 1 is a schematic sectional view of an eye of a patient who is in a lateral position lying on his/her side, illustrating a conventional surgical procedure for correcting retinal detachment.
Figure 2:
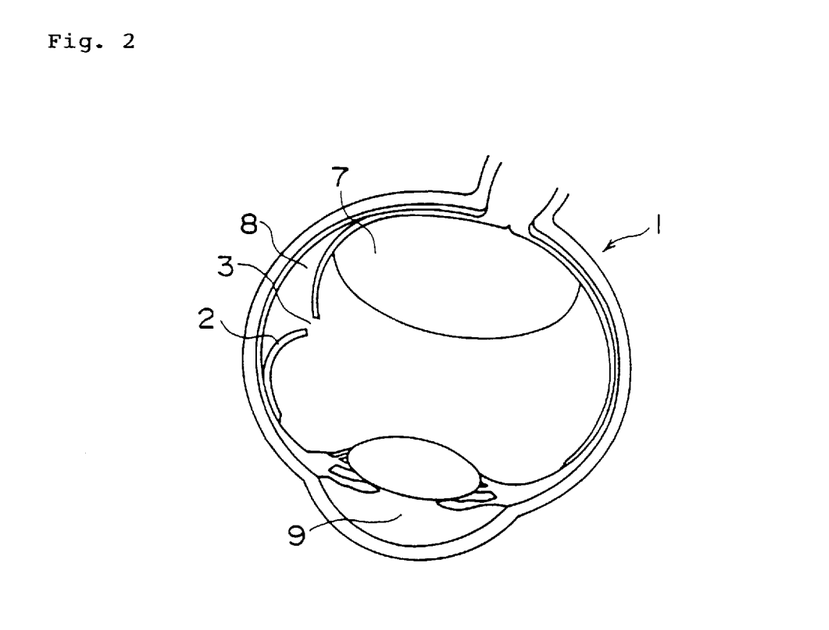
FIG. 2 is a schematic sectional view of the eye of the patient who is in a face-down position, illustrating the conventional surgical procedure for correcting retinal detachment.
Figure 3:
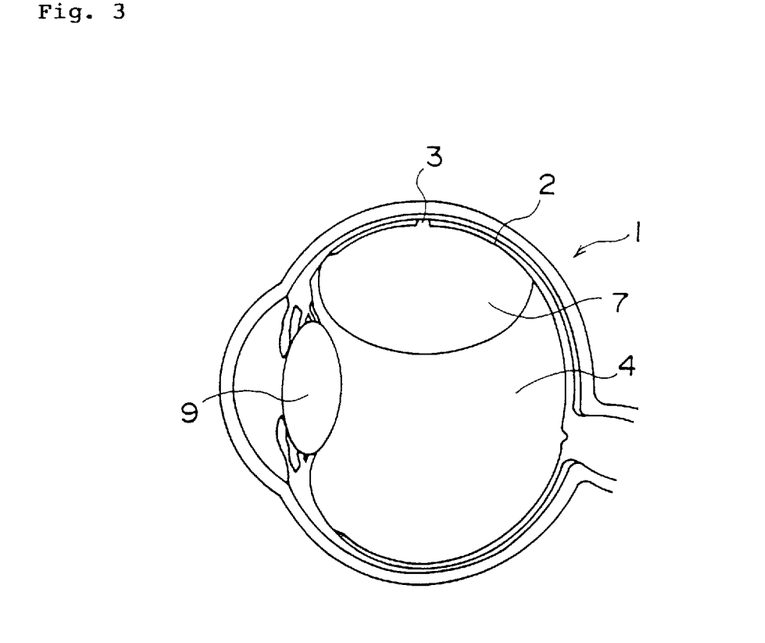
FIG. 3 is a schematic sectional view of the eye of the patient who is in a lateral position lying on his/her side, illustrating the conventional surgical procedure for correcting retinal detachment.
Figure 4:
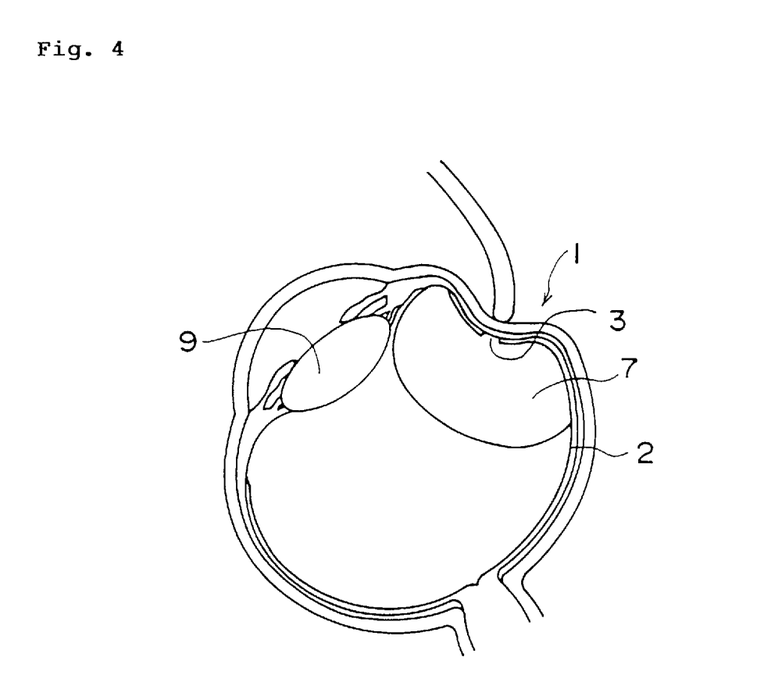
FIG. 4 is a schematic sectional view of the eye illustrating the conventional surgical procedure for correcting retinal detachment.

FIG. 1 shows a schematic sectional view of an eye 1 of a patient who is in a lateral position lying on his/her side and receiving a conventional surgical procedure. As shown in FIG. 1, while a retinal lacuna 3 is positioned at the lower side in this Figure, a needle 6 is inserted into the central portion of a vitreous body 4 from a ciliary flat portion 5. While a gas 7 (for example, a gas mixture of SF6 and air mixed at 2:3) is being injected through the needle 6, a subretinal fluid 8 is drained into the vitreous body 4. Next, the patient gradually changes his/her lateral position to a face-down position so as to move the gas 7 away from the retinal lacuna 3. FIG. 2 shows a schematic sectional view of the eye 1 of the patient who is in a face-down position and receiving the conventional surgical procedure. Subsequently, the patient shifts his/her body position and cephalic presentation so that the retinal lacuna 3 comes to the highest position as shown in FIG. 3, which shows a schematic sectional view of the eye 1 of the patient who is in a lateral position and receiving the conventional surgical procedure, whereby the remaining subretinal fluid 8 is drained into the vitreous body 4 by a single bubble (the gas 7) to thereby close the retinal lacuna 3. After a predetermined period of time (for example about 1 week) following the surgery, if restoration of the retina is confirmed, the periphery of the retinal lacuna 3 is coagulated (FIG. 4).

As described above, the conventional surgical procedure uses a gas bubble to block a retinal lacuna, and therefore, a surgeon must be highly skilled, and a patient is heavily burdened with remaining in a fixed position for about one week following the surgery until the retina is completely restored.

SUMMARY OF THE INVENTION

In view of the foregoing, the inventors of the present invention have carried out extensive studies, and finally came to have the idea of using, in retinal detachment surgery, a balloon which conventionally has been used only as a cardiac catheter or a catheter for use with blood vessels and alimentary canals such as esophagus. In short, a balloon is inserted into an eye, and a gas is injected into the inserted balloon. This surgical procedure allows the retina to be more readily restored, lightens a burden imposed on a surgical patient, and permits the surgical patient to move freely at a relatively earlier stage following surgery. Based on these findings, the present invention has been accomplished.

Accordingly, a general object of the present invention is to provide an intraocular balloon and associated devices enabling a surgeon to readily perform an operation for correcting retinal detachment and to lighten a burden imposed on a surgical patient to a great extent, as well as to provide a surgical procedure for retinal detachment using such devices.

The present invention provides an intraocular balloon having a gas injection valve for injecting a gas therethrough.

The present invention provides an intraocular balloon insertion guide for guiding the intraocular balloon into an eye.

The present invention provides a holder having an insertion portion for holding a balloon or the like and a sutural portion for fixing the holder onto the surface of an eye.

The present invention provides a surgical procedure for retinal detachment, comprising the steps of:

removing a vitreous body from an eye;

feeding an intraocular perfusate into the eye;

inserting into the eye an intraocular balloon insertion guide which holds an intraocular balloon and is held by a holder;

suturing the holder onto the eye for fixation;

removing the intraocular balloon insertion guide;

injecting a gas into the intraocular balloon while the intraocular perfusate is drained from the eye, so as to press a retinal lacuna by the intraocular balloon;

closing the retinal lacuna; and feeding the intraocular perfusate into the eye while the gas is discharged from the intraocular balloon.

The above and other objects, features, and advantages of the present invention will become apparent from the following description and the appended claims, taken in conjunction with the accompanying drawings.

DESCRIPTION OF THE PREFERRED EMBODIMENTS

Figure 5:
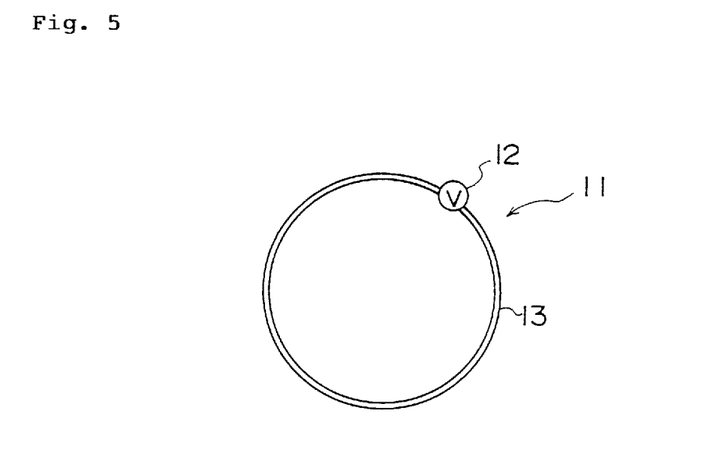
FIG. 5 is a schematic view of an intraocular balloon according to an embodiment of the present invention showing an inflated state established by injection of a gas.

Embodiments of the present invention will now be described with reference to the drawings. An intraocular balloon of the invention is used, for example, to close a retinal lacuna to thereby restore the retina. As shown in FIG. 5, an intraocular balloon 11 has a gas injection valve 12, through which a gas is injected into the intraocular balloon 11 from the exterior thereof to thereby inflate the balloon 11. FIG. 5 shows the intraocular balloon 11 inflated by an injected gas.

Figure 6:
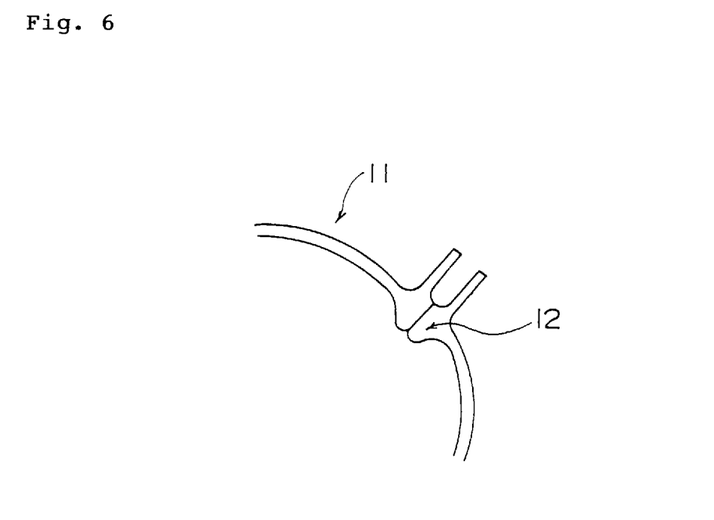
FIG. 6 is a schematic longitudinal sectional view of a gas injection valve of the intraocular balloon of the embodiment.
Figure 7:
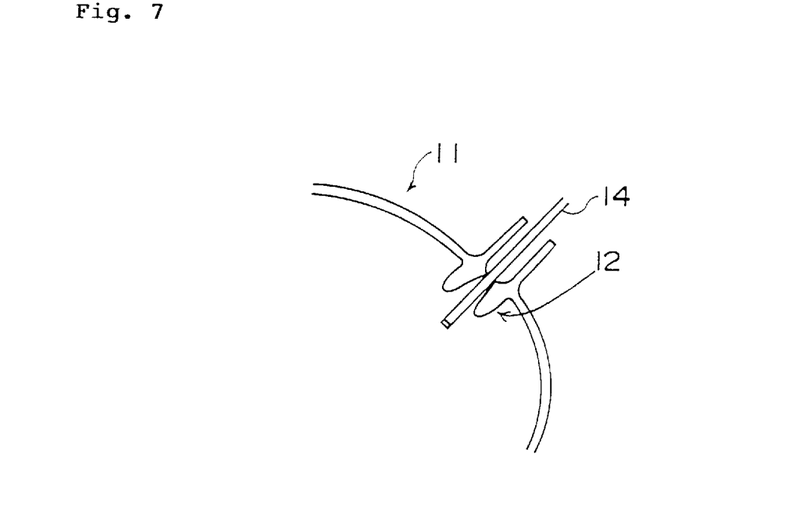
FIG. 7 is a schematic longitudinal sectional view of the gas injection valve of the intraocular balloon of the embodiment showing a state of a gas injection tube or a laser probe being inserted through the gas injection valve.

In order to prevent an injected gas from being released from the intraocular balloon 11, the gas injection valve 12 is preferably a check valve. Such a check valve has a shape, for example, as shown in FIGS. 6 and 7, and is made of an elastic material. The check valve structure confines a gas injected through the gas injection valve 12 to within the intraocular balloon 11 (FIG. 6). For example, when a gas injection tube 14 is inserted into the intraocular balloon 11, the gas injection valve 12 closely contacts the gas injection tube 14 to thereby prevent the injected gas from escaping from the intraocular balloon 11 (FIG. 7). Subsequently, when the gas injection tube 14 is removed, the gas injection valve 12 closes hermetically to confine the injected gas within the intraocular balloon 11. In order to coagulate the peripheral area of a retinal lacuna by a laser beam, the gas injection valve 12 also allows a laser probe 14 to be inserted or removed therethrough.

The gas injection valve 12 may also have a structure similar to that of a butterfly valve.

In view of easy handling, strength, safety, and laser beam transmission, the shell (hereafter referred to as the membrane) of the intraocular balloon 11 is preferably made of natural latex rubber; a synthetic latex rubber such as styrene-butadiene rubber, acrylonitrile-butadiene rubber, or chloroprene rubber; or a polyolefin-based copolymer resin such as an ethylene-propylene copolymer resin, an ethylene-butadiene copolymer resin, an ethylene-acrylonitrile copolymer resin, or an ethylene-vinyl acetate resin. The material of the gas injection valve 12 may be identical to or different from that of the remainder of the intraocular balloon 11.

In view of easy handling, strength, safety, and laser beam transmission, the thickness of the intraocular balloon is 0.01 to 0.3 mm, preferably 0.03 to 0.27 mm, more preferably 0.05 to 0.24 mm.

In order that a patient be permitted to freely move within a relatively short period of time following surgery, it is necessary for the membrane of the intraocular balloon 11 to press substantially the entire retina including a retinal lacuna. However, if the intraocular balloon 11 inflated by an injected gas is substantially spherical, it is highly likely to contact the lens. The contact of the lens with foreign matter such as a gas will induce a cataractogenic change in the lens within a short period of time, causing opacity of the lens or the loss of transparency of the lens. Accordingly, after being inflated by injection of a gas, the intraocular balloon 11 preferably has a depression to avoid contact with the lens.

Figure 8:
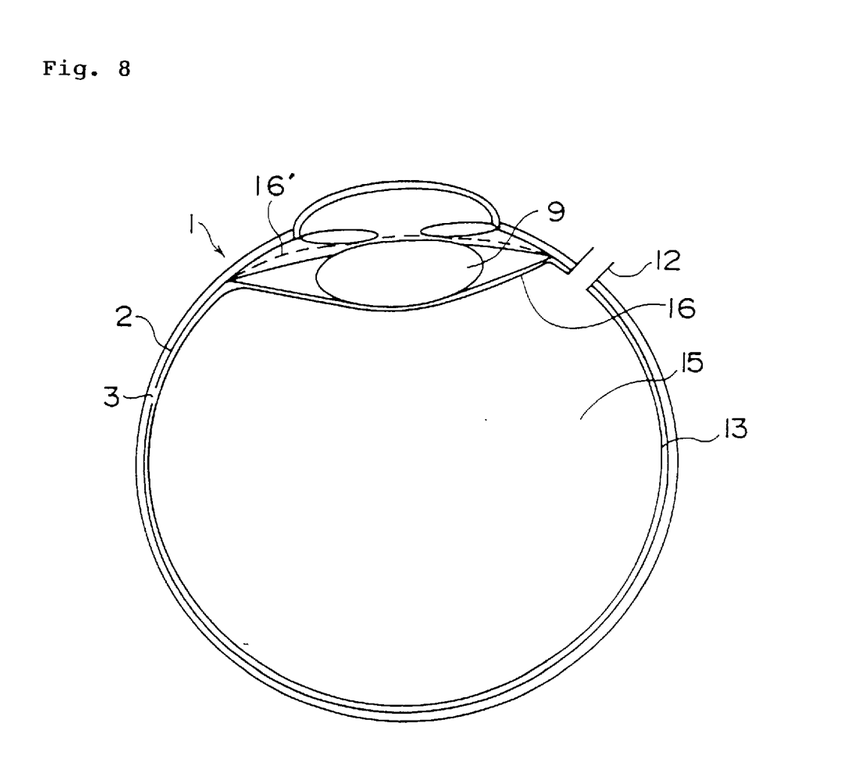
FIG. 8 is a schematic view showing an intraocular balloon inserted within an eye and inflated by an injected gas.

FIG. 8 shows the above-mentioned situation that must be avoided, wherein an intraocular balloon 15 which has a substantially spherical shape is inflated within an eye by an injected gas. As shown in FIG. 8, the inflated intraocular balloon 15 presses substantially an entire retina 2 including a retinal lacuna 3, but at the same time, a part 16 of the membrane of the intraocular balloon 15 is in contact with a lens 9. A dashed line 16' indicates the part 16 of the intraocular balloon membrane which would be shaped if the lens 9 were absent.

To prevent the inflated intraocular balloon 15 from contacting the lens 9, the intraocular balloon 15 preferably has a depression 17 so that it closes the retinal lacuna 3 but avoids contacting the lens 9.

Figure 10:
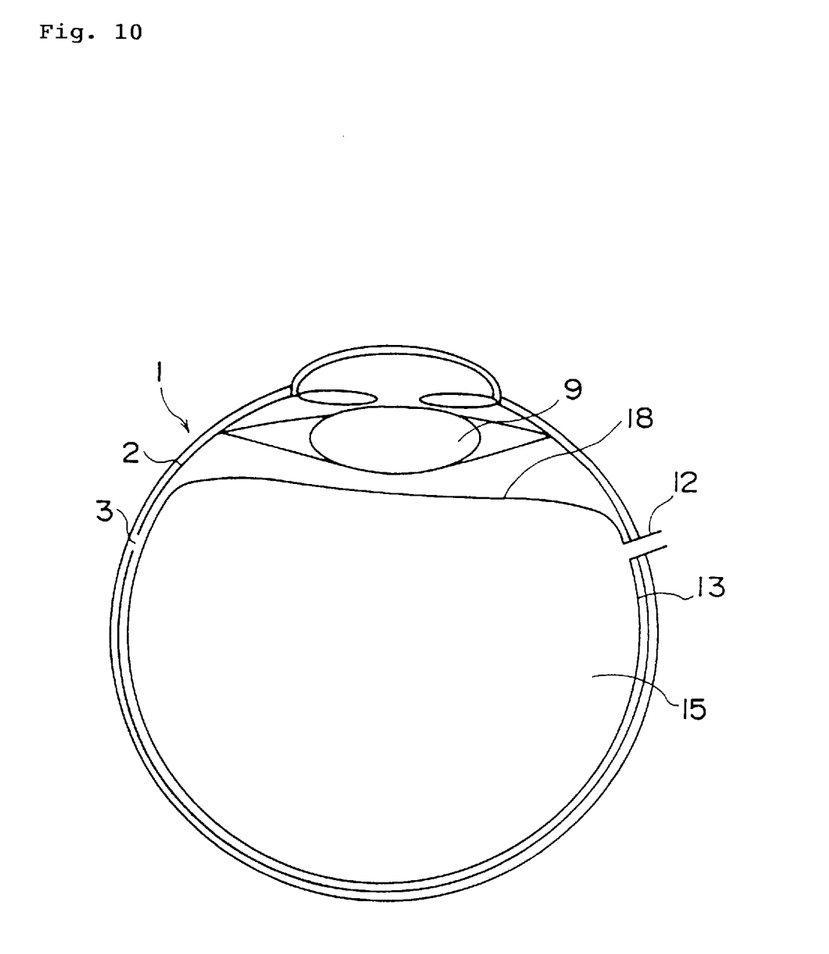
FIG. 10 is a schematic view showing an intraocular balloon according to another embodiment of the present invention, which intraocular balloon is inserted within an eye and inflated by an injected gas.
Figure 11:
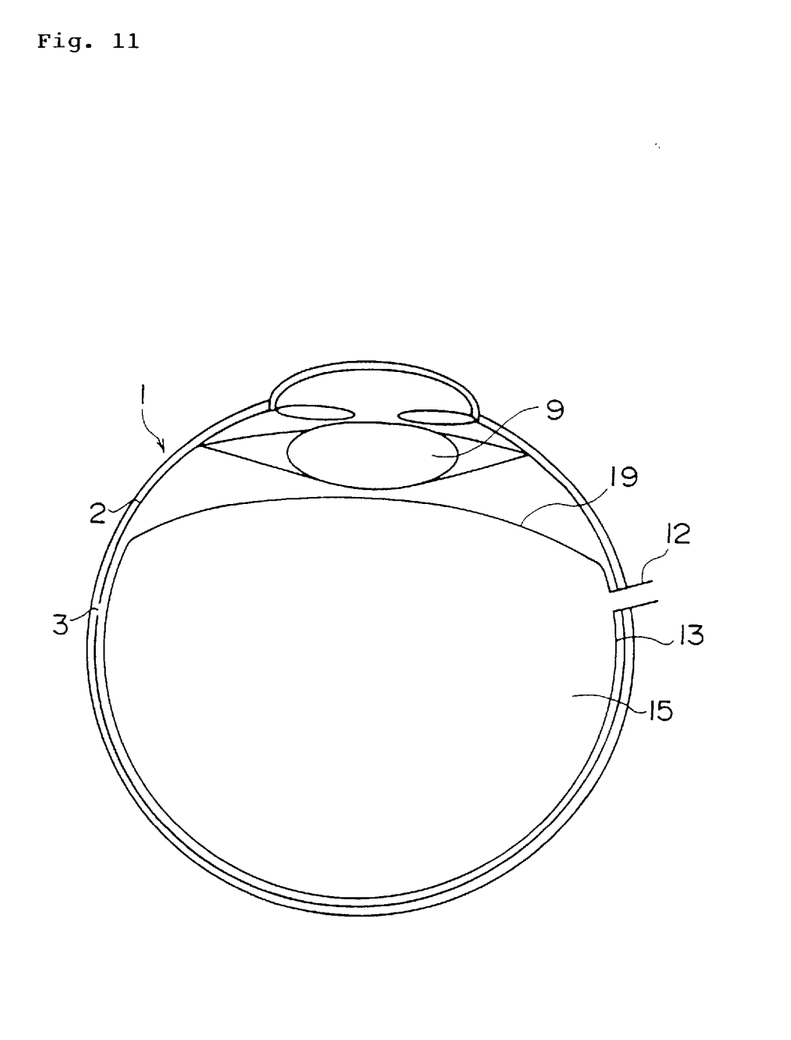
FIG. 11 is a schematic view showing an intraocular balloon according to still another embodiment of the present invention, which intraocular balloon is inserted within an eye and inflated by an injected gas.
Figure 12:
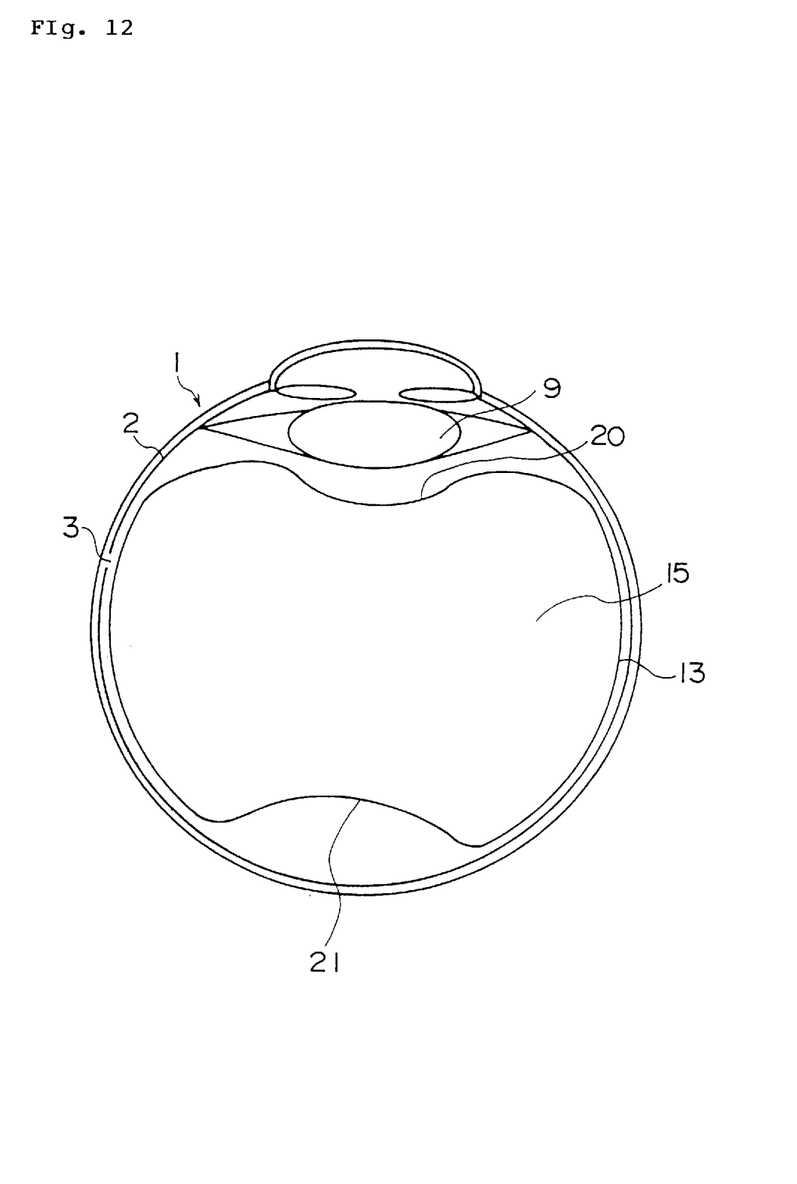
FIG. 12 is a schematic view showing an intraocular balloon according to a further embodiment of the present invention, which intraocular balloon is inserted within an eye and inflated by an injected gas.

Here, the term "depression" denotes part of an intraocular balloon which is deformed due to predetermined means employed on the intraocular balloon so as to avoid contact with the lens upon inflation of the intraocular balloon, which would otherwise assume a substantially spherical shape when inflated by an injected gas. Accordingly, as shown in FIG. 10, a portion 18 which assumes a substantially flat shape upon inflation of the intraocular balloon 15 is classified as a depression. Also, as shown in FIG. 11, a portion 19 which assumes a convex shape upon inflation of the intraocular balloon 15 and which has a greater radius of curvature than the rest of the intraocular balloon 15 also is classified as a depression. Further, as shown in FIG. 12, in addition to a depression 20, a depression 21 not corresponding to the lens may be formed upon inflation of the intraocular balloon 15.

In view of safety, the distance between such a depression and the lens is not less than 0.5 mm, preferably not less than 0.7 mm.

Figure 9:
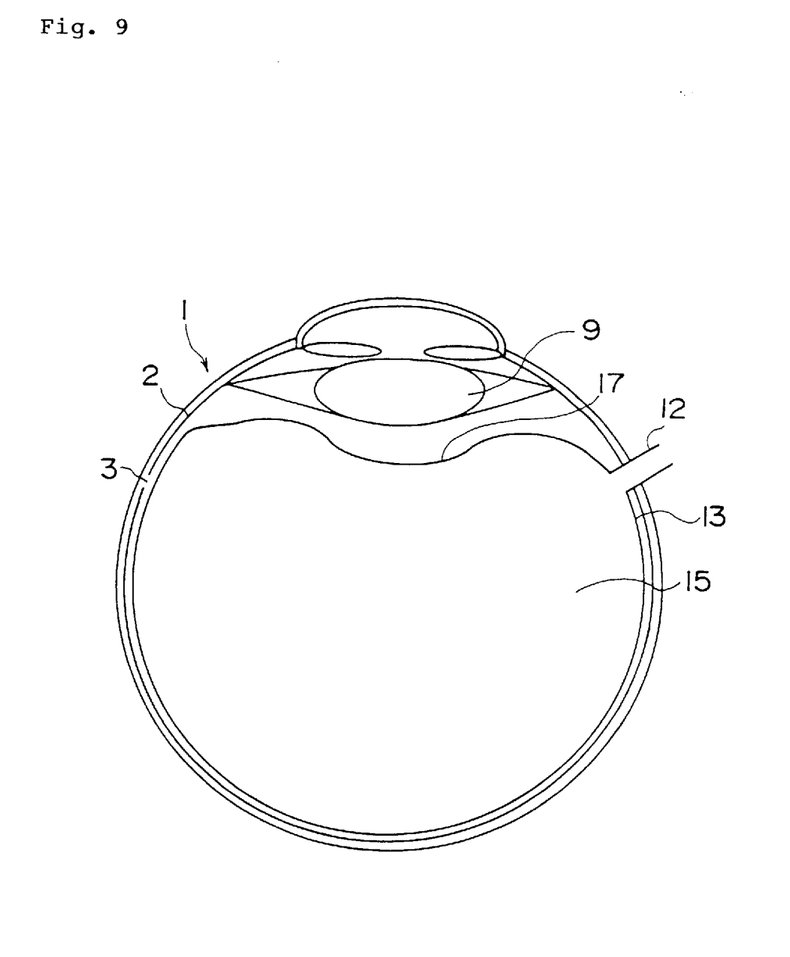
FIG. 9 is a schematic view showing an intraocular balloon according to an embodiment of the present invention, which intraocular balloon is inserted within an eye and inflated by an injected gas.

Next will be described several means for forming a depression in a gas-inflated intraocular balloon. First means is to make that portion of an intraocular balloon which is expected to become a depression thicker than the remainder of the intraocular balloon. This means presents difficulty in forming the concave depression 17 shown in FIG. 9, but can be used to form the substantially flat depression 18 shown in FIG. 10 or the convex depression 19 shown in FIG. 11.

Second means is to affix a depression-forming member onto that portion of an intraocular balloon which is expected to become a depression. The coverage of the depression-forming member may extend beyond the depression portion if a retinal lacuna can be closed. Material for the depression-forming member may be identical to or different from that for an intraocular balloon.

Third means is a deformable supporting member, one end of which is fixed onto the inner surface of an intraocular balloon at that portion which is expected to become a depression and the other end of which is fixed onto the inner surface of the intraocular balloon at a portion substantially opposed to the depression portion. "Deformable supporting member" means that the supporting member does not induce a force (tension) of inwardly pulling the intraocular balloon before the intraocular balloon is gas-inflated, and induces a force of inwardly pulling the intraocular balloon when the intraocular balloon is gas-inflated to press substantially the entire retina including a retinal lacuna. Examples of material for such a deformable supporting member include natural fibers such as silk and wool, regenerated fibers such as rayon, semisynthetic fibers such as acetate rayon, and synthetic fibers such as polyester and nylon. A single or more than one supporting member made of such material and having a predetermined length is fixed within an intraocular balloon.

Such a deformable supporting member is preferably elastic, like rubber, for convenience of adjusting the shape of a depression in accordance with the thickness of the lens.

The above-described first, second, and third means may be used in combination.

Preferably, a second membrane having a fluid inlet is attached onto the intraocular balloon membrane through fixation at one or more points. When the intraocular balloon is removed from an eye after a retinal lacuna is closed, an intraocular filler fluid (intraocular perfusate) is injected into the eye through the fluid inlet in order to maintain constant an intraocular pressure. While a gas is being removed from the intraocular balloon, an intraocular perfusate is injected into the eye through the gap between the intraocular balloon membrane and the second membrane to thereby maintain constant an intraocular pressure. Since this arrangement establishes a laminar flow of the intraocular perfusate when the intraocular perfusate is injected into the eye, inflow of the intraocular perfusate does not cause any impairment to the retina or other telae (for example, a closed retinal lacuna cleaves again).

Figure 13:
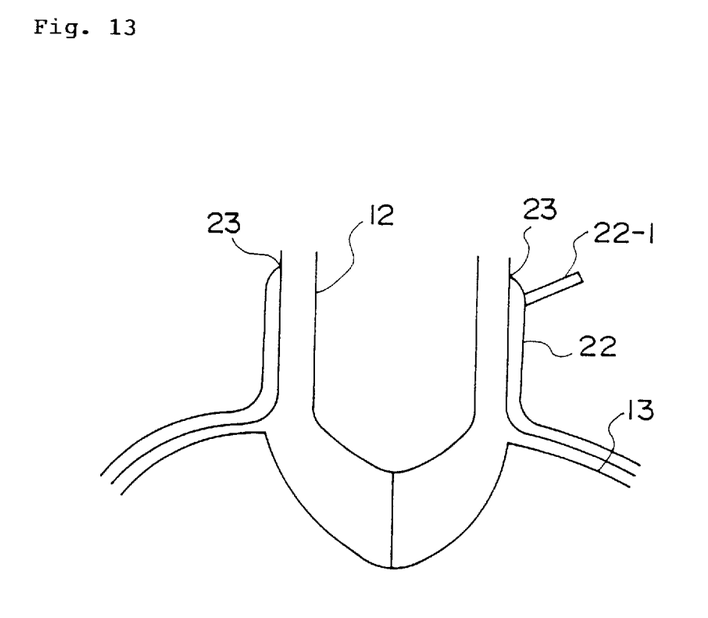
FIG. 13 is a longitudinal sectional view of an intraocular balloon according to an embodiment of the present invention showing a gas injection valve and a second membrane a part of which is attached onto the periphery of the gas injection valve and which has a fluid inlet.

Preferably, in view of safety, part of the above-described second membrane is coaxially attached onto the periphery of a gas injection valve, so that there is no need for incising an eye at a different position to form a fluid inlet. FIG. 13 shows the gas injection valve 12 and a second membrane 22 having a fluid inlet 22-1 which is attached onto a membrane 13 of an inflated intraocular balloon such that part of the second membrane 22 is coaxially attached onto the periphery 23 of the gas injection valve 12.

Preferably, the fluid inlet 22-1 is fixed to the second membrane 22 and arranged such that it is located outside an eye when an intraocular balloon is inserted into an eye. The fluid inlet 22-1 preferably has a check valve structure or is made of rubber-like material, because it must be opened only when a fluid is injected therethrough with a syringe or the like and be closed for any other occasions.

In order to avoid contact with the lens, the second membrane, like an intraocular balloon, is preferably constructed so as to form a depression therein when the intraocular balloon is gas-inflated.

In view of safety, the distance between the depression of the second membrane and the lens is not less than 0.3 mm, preferably not less than 0.5 mm.

The second membrane may be such that when an intraocular balloon is gas-inflated it covers substantially the entirety, about half, or only a part of the intraocular balloon.

The membrane of an intraocular balloon and the second membrane are spot-joined, for example, by fusion. A method other than fusion may also be acceptable. Also, there is no restriction on means for joining the second membrane and the gas injection valve of an intraocular balloon.

Figure 14:
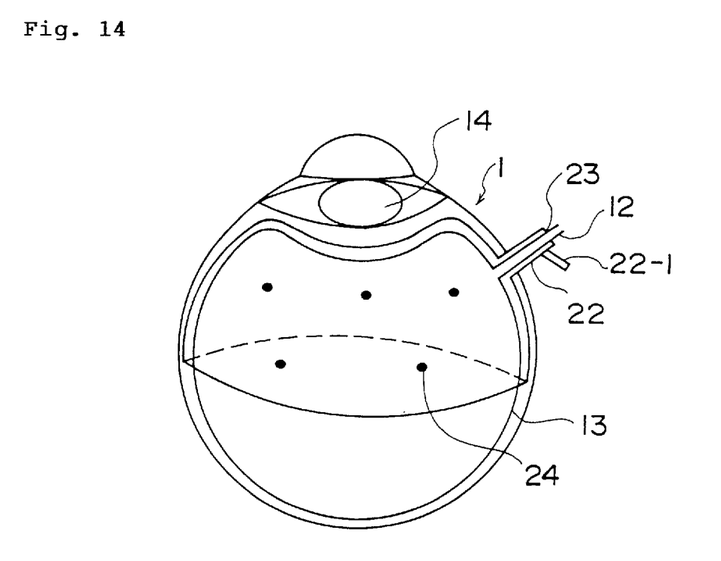
FIG. 14 is a schematic view showing an intraocular balloon according to an embodiment of the present invention onto which the second membrane is attached.

FIG. 14 shows an intraocular balloon onto which the second membrane is attached and gas-inflated within an eye. In FIG. 14, the second membrane 22 is spot-fused onto the membrane 13 of an intraocular balloon at points 24. Part of the second membrane 22 is attached onto a periphery 23 of the gas injection valve 12. The second membrane 22 covers substantially half of the intraocular balloon. The fluid inlet 22-1 is fixed to the second membrane 22.

A surgical procedure using the intraocular balloon of the present invention will next be described. The outer surface (sclera) of an eyeball is incised at a superior position located about 4 to 4.5 mm away from the corneal ring, the incision having a length of about 2 mm in parallel with the corneal ring. A cilinary flat portion (located about 3.5 to 4.5 mm away from the corneal ring) within the superior part of the eyeball is incised about 2 mm long. A vitreous body cutter, for example, is inserted through the exterior incision. While a subretinal fluid is being drained into the vitreous body, the vitreous body is incised and drawn out (through a flute needle, for example). At the same time, an intraocular perfusate is injected into the eye through the interior incision to thereby maintain constant an intraocular pressure (for example, at about 20 to 30 mmHg).

Next, either the above-described exterior or interior incision is further incised to a length of about 4 mm. An intraocular balloon is inserted into the eye through the extended incision. Preferably, an intraocular balloon insertion guide which holds the intraocular balloon is used for insertion of the intraocular balloon. The intraocular balloon insertion guide will facilitate direct insertion of the soft intraocular balloon into the eye through the incision.

Figure 15:
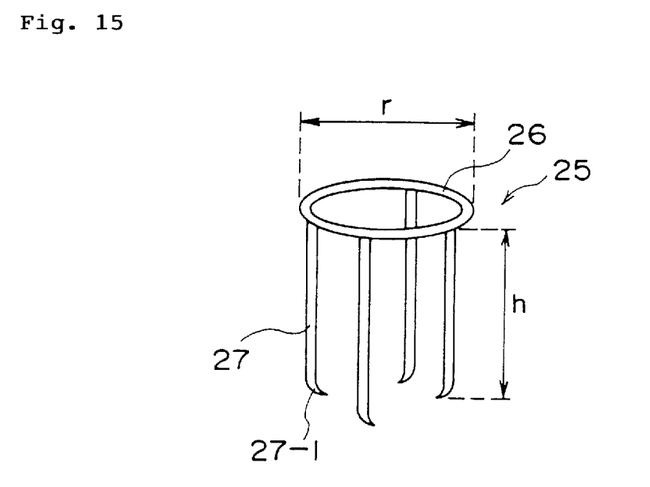
FIG. 15 is a schematic view showing an intraocular balloon insertion guide according to an embodiment of the present invention.

The intraocular balloon insertion guide has a structure, for example, as shown in FIG. 15. An intraocular balloon insertion guide 25 includes legs 27 serving as a guide for an intraocular balloon and a ring 26 for fixing the legs 27 in place. An intraocular balloon is held in the space surrounded by the legs 27. Subsequently, the intraocular balloon insertion guide 25 which thus holds the intraocular balloon is inserted into an eye, thereby facilitating insertion of the intraocular balloon. Preferably, diameter r of the ring 26 is substantially as large as the size of an incision (about 4 to 5 mm, for example). Length h of the legs 27 depends on the size of an intraocular balloon, but must be smaller than the size of an eye, preferably about not more than 20 mm, for example. In FIG. 15, the legs 27 extend vertically from the ring 26, but may extend in such a manner as to incline inward, i.e. toward the interior of the intraocular balloon insertion guide 25. Also, in FIG. 15, end 27-1 of the legs 27 are bent inward, but may be straight or bent outward if there is no risk of damaging intraocular telae. Further, in FIG. 15, the number of the legs 27 is four, but is not limited thereto.

It may be 2 to 10, preferably 3 to 8. Any material is acceptable for the intraocular balloon insertion guide if it is not likely to break, has such a hardness as to not damage intraocular telae, and is excellently safe. Examples of such material include polypropylene and polymethyl methacrylate, which are used as materials for medical devices. The legs and the ring may be integrally formed or may be formed separately and then joined together.

Figure 16:
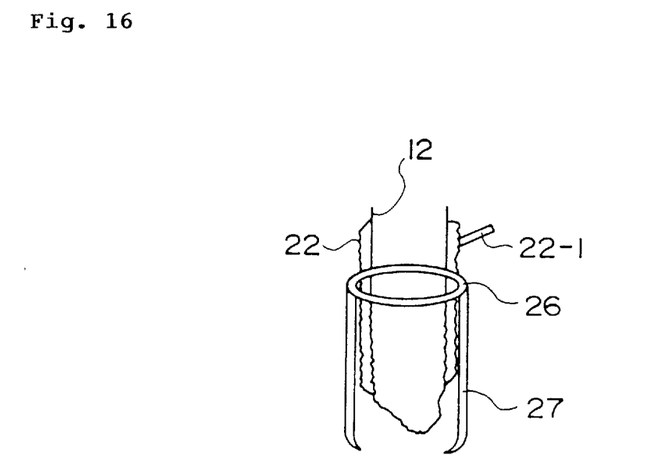
FIG. 16 is a schematic view showing how an intraocular balloon is held in the intraocular balloon insertion guide of FIG. 15.

FIG. 16 schematically illustrates how an intraocular balloon is held in the above-described intraocular balloon insertion guide. Because of no injection of a gas, the intraocular balloon and the second membrane 22 are held within the legs 27 in a shriveled state.

After the intraocular balloon, together with the intraocular balloon insertion guide, is inserted into an eye, the intraocular balloon insertion guide can be readily removed from inside the eye merely by pulling out the ring.

The intraocular balloon inserted into the eye is preferably held by a holder which is fixed onto an eyeball, to thereby prevent the intraocular balloon from moving or rotating during and following surgery. More preferably, the holder is constructed such that it can also hold the intraocular balloon insertion guide in order to attain smooth insertion of the intraocular balloon into the eye. The holder has insertion slits for holding the intraocular balloon insertion guide whose legs are inserted through the slits, an insertion hole for holding the intraocular balloon which is inserted through the hole, and suture portions at which the holder is sutured onto the eyeball surface to thereby fix the holder onto the eyeball. Any material, either transparent or opaque, is acceptable for the holder if it is medically applicable. Examples of such material include plastics such as polypropylene and polymethyl methacrylate.

Figure 17:
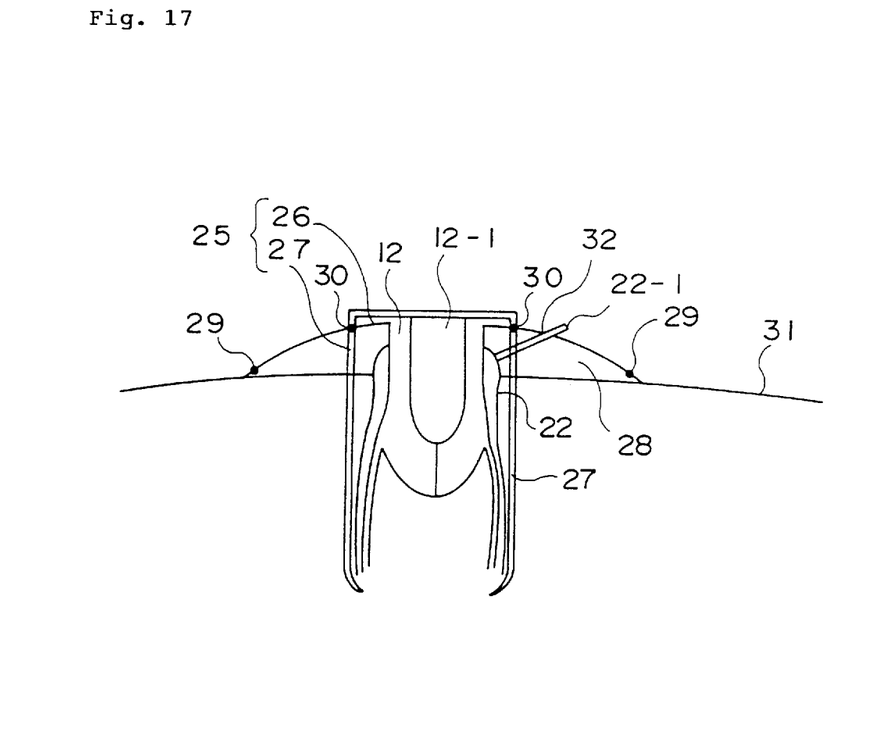
FIG. 17 is a longitudinal sectional view showing schematically a holder according to an embodiment of the present invention which holds an intraocular balloon and an intraocular balloon insertion guide, both inserted into an eye, and which is sutured onto an eyeball.
Figure 18:
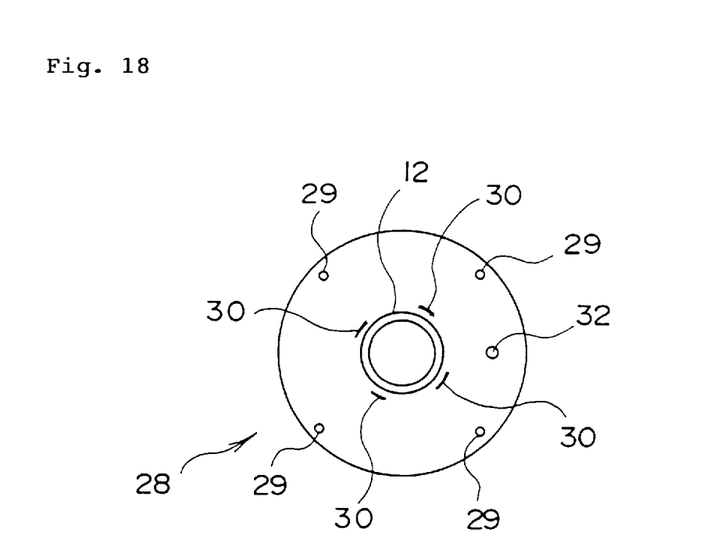
FIG. 18 is a plan view of the state illustrated in FIG. 17.
Figure 19:
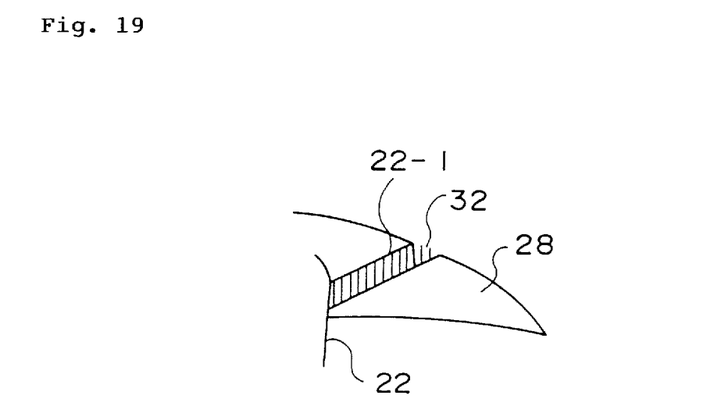
FIG. 19 is a partially enlarged view of that portion of the holder according to the embodiment where a fluid inlet is inserted.

FIG. 17 is a longitudinal sectional view showing schematically the holder which holds the intraocular balloon and the intraocular balloon insertion guide, both inserted into an eye, and which is sutured onto an eyeball. FIG. 18 is a schematic plan view showing the state illustrated in FIG. 17. In FIGS. 17 and 18, a holder 28 is fixed onto an eyeball surface 31 (sclera surface) through a plurality of suture portions 29 (for example, about 2 to 10 suture portions, preferably 3 to 8 suture portions, and more preferably 4 to 6 suture portions) located in the vicinity of the edge portion of the holder 28. The holder 28 has an insertion hole for holding the gas injection valve 12 which is inserted through the hole. The fluid inlet 22-1, through which a fluid injection syringe is inserted, penetrates the holder 28 at a portion 32. The legs 27 of the intraocular balloon insertion guide 25 are inserted through insertion slits 30 formed in the holder 28 to thereby hold the intraocular balloon insertion guide 25 by the holder 28. Since the intraocular balloon is held by the intraocular balloon insertion guide 25, which in turn is held by the holder 28, the intraocular balloon can be readily inserted into an eye. After the intraocular balloon is inserted into the eye, the intraocular balloon insertion guide 25 can be readily removed from the holder 28 through removal of the legs 27 through the insertion slits 30. FIG. 19 shows a partially enlarged view of that portion of the holder 28 where the fluid inlet 22-1 is inserted. The hole of the portion 32 preferably has a diameter that allows a needle of 27G to 30G to go through. The fluid inlet 22-1 may project into the exterior of the holder 28 (FIG. 17) or may be flush with the holder 28 (FIG. 19).

Next, the gas injection valve is connected to a gas (for example, air) source such as a gas cylinder via a joint or the like. The gas is injected into the intraocular balloon while the intraocular perfusate is being drained from the eye, to thereby maintain constant an intraocular pressure. When the intraocular balloon is inflated to press substantially the entire retina including a retinal lacuna, injection of the gas is terminated. The inflated intraocular balloon preferably does not contact the lens (FIGS. 9 to 12).

Subsequently, the gas source such as a gas cylinder is disconnected from the joint or the like. A laser probe for intraocular photocoagulation is inserted into the intraocular balloon through the joint and the gas injection valve. Then, the periphery of the retinal lacuna is coagulated to close the retinal lacuna, and subsequently the laser probe is removed from the intraocular balloon. If the gas injection valve is a check valve, the gas will not be released from the intraocular balloon even after the laser probe is removed. After the surgery, in order to confine the gas securely within the intraocular balloon, the opening of the gas injection valve is preferably plugged.

Since the gas injection valve of the intraocular balloon is fixed onto the eyeball via the holder, and the closed retinal lacuna is pressed by the intraocular balloon, the patient is allowed to move freely within a relatively short period of time following the surgery.

After the elapse of a predetermined period of time, the gas is released from the intraocular balloon, and the intraocular balloon is removed from the eye. In order to release the confined gas, a flute needle or a like release tube is inserted into the intraocular balloon. If the gas is hastily released from the intraocular balloon, an intraocular pressure will become negative, resulting in a possible damage to intraocular telae. Accordingly, in order to maintain constant the intraocular pressure, release of the gas from the intraocular balloon and injection of the intraocular perfusate into the eye are controlled adequately. If the fluid inlet is made of rubber-like material, a syringe or a like device may be inserted into the fluid inlet to inject the intraocular perfusate into the eye, and after removal of the syringe, the injected intraocular perfusate can be prevented from flowing out of the eye.

As described above, the intraocular balloon of the invention enables a surgeon to readily perform an operation for retinal detachment and significantly lightens a burden imposed on a surgical patient. Through formation of the intraocular balloon into a predetermined shape, a lens can be prevented from suffering a cataractogenic change. Also, through attachment of a second membrane onto the intraocular balloon, there can be prevented damage to an intraocular tela when the intraocular balloon is removed from an eye.

The intraocular balloon insertion guide of the invention facilitates insertion of the intraocular balloon into an eye. Further, the holder of the invention prevents the intraocular balloon from moving or rotating during or following surgery.

What is claimed is:
1. An intraocular balloon comprising:
a generally spherical first balloon configured so as to be introduced into an eye; and
a fluid injection valve mounted relative to said first balloon such that a fluid may be introduced into said first balloon via said fluid injection valve to inflate the first balloon when the first balloon is introduced into the eye,
wherein said first balloon has a depression located thereon at such a position that said first balloon does not contact the lens of the eye when the first balloon is introduced into the eye and inflated.

2. The intraocular balloon according to claim 1, wherein the fluid injection valve is a check valve.

3. The intraocular balloon according to claim 1, wherein the fluid injection valve allows insertion and removal of a laser probe.

4. The intraocular balloon according to claim 1, wherein the thickness of the first balloon is from 0.01 to 0.3 mm.

5. The intraocular balloon according to claim 1, wherein the material of the first balloon is latex rubber or a polyolefin-based copolymer resin.

6. The intraocular balloon according to claim 1, wherein the distance between the depression and the lens is not less than 0.5 mm.

7. The intraocular balloon according to claim 1, wherein the depression is formed so as to be thicker than the remainder of the first balloon.

8. The intraocular balloon according to claim 1, wherein the depression is formed by affixing a depression-forming member onto the portion of an intraocular balloon corresponding to the depression.

9. The intraocular balloon according to claim 1, wherein the depression is formed by means of a deformable supporting member, one end of which is fixed onto the inner surface of a first balloon at the portion corresponding to the depression and the other end of which is fixed onto the inner surface of the intraocular balloon at a portion substantially opposed to the depression.

10. The intraocular balloon according to claim 9, wherein the supporting member is made of an elastic material.

11. The intraocular balloon according to claim 1, which further includes a second membrane having a separate fluid inlet, the second membrane being attached onto the membrane of the intraocular balloon through fixation at one or more points.

12. The intraocular balloon according to claim 11, wherein the second membrane is coaxially attached onto the periphery of the fluid injection valve.

13. The intraocular balloon according to claim 11, wherein the second membrane is constructed to form a depression therein so as to avoid contact of the second membrane with the lens when the intraocular balloon is inflated.

14. The intraocular balloon according to claim 11, wherein the distance between the depression of the second membrane and the lens is not less than 0.3 mm.

15. An intraocular balloon comprising:

a generally spherical first balloon configured so as to be introduced into an eye; and a fluid injection valve mounted relative to said first balloon such that a fluid may be introduced into said first balloon via said fluid injection valve to inflate the first balloon when the first balloon is introduced into the eye, wherein said first balloon has a depression located thereon at such a position relative to said fluid injection valve that said first balloon does not contact the lens of the eye when the first balloon is introduced into the eye and inflated.

16. An intraocular balloon holder for holding an intraocular balloon in an eye via an insertion guide, the intraocular balloon comprising a generally spherical first balloon configured so as to be introduced into an eye and a fluid injection valve mounted relative to said first balloon such that a fluid may be introduced into said first balloon via said fluid injection valve to inflate the first balloon when the first balloon is introduced into the eye, the insertion guide comprising legs serving as a guide for the intraocular balloon and a ring for fixing the legs in place, the intraocular balloon holder comprising:

a material positioned at an exterior surface of the eye;

an insertion hole formed at a central portion of the material, through which the intraocular balloon may be inserted into the eye;

insertion slits formed at the central portion of the material, the legs of the insertion guide being fittable in the insertion slits; and suture portions at the periphery of the holder for fixing the holder to the eye.

17. A surgical procedure for correcting retinal detachment, comprising the steps of:

removing a vitreous body from an eye;

feeding an intraocular perfusate into the eye;

inserting into the eye an intraocular balloon insertion guide which holds an intraocular balloon and is held by a holder;

suturing the holder onto the eye for fixation;

removing the intraocular balloon insertion guide;

injecting a fluid into the intraocular balloon while the intraocular perfusate is drained from the eye, so as to press a retinal lacuna by the intraocular balloon against the retina;

closing the retinal lacuna; and feeding the intraocular perfusate into the eye while the gas is discharged from the intraocular balloon.

18. The surgical procedure according to claim 17, wherein the retinal lacuna is closed through use of laser beams.

19. An insertion guide for guiding an intraocular balloon into an eye, the intraocular balloon comprising a generally spherical first balloon configured so as to be introduced into an eye, and a gas injection valve mounted relative to said first balloon such that a fluid may be introduced into said first balloon via said gas injection valve to inflate the first balloon when the first balloon is introduced into the eye, the insertion guide comprising:

legs serving as a guide for the intraocular balloon; and a ring for fixing the legs in place.

* * * * *

UNITED STATES PATENT AND TRADEMARK OFFICE
CERTIFICATE OF CORRECTION

PATENT NO. : 5,846,258
DATED : December 8, 1998
INVENTOR(S) : YOSHINORI TAKAYANAGI ET AL It is certified that error appears in the above-identified patent and that said Letters Patent is hereby corrected as shown below:

IN THE CLAIMS

Column 10, line 38, in claim 17, change "gas" to --fluid--.

Signed and Sealed this

First Day of June, 1999

Attest:

Attesting Officer

Q. TODD DICKINSON

Acting Commissioner of Patents and Trademarks